(12) United States Patent
Koshida

(10) Patent No.: US 9,402,423 B2
(45) Date of Patent: Aug. 2, 2016

(54) LEG WEAR

(71) Applicant: OKAMOTO CORPORATION, Koryo-cho, Kitakatsuragi-gun, Nara (JP)

(72) Inventor: Yoshinori Koshida, Nara (JP)

(73) Assignee: OKAMOTO CORPORATION, Koryo-Cho, Kitakatsuragi-Gun, Nara (JP)

( * ) Notice: Subject to any disclaimer, the term of this patent is extended or adjusted under 35 U.S.C. 154(b) by 42 days.

(21) Appl. No.: 14/046,318

(22) Filed: Oct. 4, 2013

(65) Prior Publication Data

US 2015/0000009 A1  Jan. 1, 2015

(30) Foreign Application Priority Data

Jun. 27, 2013 (JP) ................. 2013-135261

(51) Int. Cl.
| | |
|---|---|
| A41B 11/00 | (2006.01) |
| A61F 13/08 | (2006.01) |
| A41B 11/14 | (2006.01) |
| A41B 11/01 | (2006.01) |

(52) U.S. Cl.
CPC .............. *A41B 11/00* (2013.01); *A41B 11/001* (2013.01); *A41B 11/002* (2013.01); *A41B 11/003* (2013.01); *A41B 11/01* (2013.01); *A41B 11/14* (2013.01); *A61F 13/08* (2013.01)

(58) Field of Classification Search
CPC ...... A41B 11/00; A41B 11/14; A41B 11/001; A41B 11/002; A41B 11/003; A41B 11/01; A61F 13/08
USPC .................................................... 2/239, 242
See application file for complete search history.

(56) References Cited

U.S. PATENT DOCUMENTS

| | | | | |
|---|---|---|---|---|
| 288,592 | A * | 11/1883 | OSborne | 2/239 |
| 1,968,832 | A * | 8/1934 | Hinchliff | 2/239 |
| 2,667,774 | A * | 2/1954 | Allen | 66/179 |
| 3,015,942 | A * | 1/1962 | Getaz | 66/186 |
| 3,146,468 | A * | 9/1964 | McDonald | 2/239 |
| 4,898,007 | A * | 2/1990 | Dahlgren | A41B 11/003 2/239 |
| 5,867,837 | A * | 2/1999 | Otto et al. | 2/239 |
| 6,139,929 | A * | 10/2000 | Hayton et al. | 428/35.2 |
| 6,158,253 | A * | 12/2000 | Svoboda et al. | 66/178 R |
| 6,935,141 | B2 * | 8/2005 | Takeda et al. | 66/187 |
| 7,971,280 | B2 * | 7/2011 | Kaneda | 2/239 |
| 2004/0261466 | A1* | 12/2004 | Takeda et al. | 66/176 |
| 2008/0034802 | A1* | 2/2008 | Hirao | A41B 11/00 66/8 |
| 2008/0041113 | A1* | 2/2008 | Mori | A41B 11/02 66/54 |
| 2009/0165190 | A1* | 7/2009 | Araki | A61F 13/064 2/240 |
| 2009/0223254 | A1* | 9/2009 | Ishida | 66/185 |

(Continued)

FOREIGN PATENT DOCUMENTS

| | | |
|---|---|---|
| JP | 3125430 U | 8/2006 |
| JP | 4590247 B2 | 12/2010 |

*Primary Examiner* — Shaun R Hurley
*Assistant Examiner* — Bao-Thieu L Nguyen
(74) *Attorney, Agent, or Firm* — Nicholas Trenkle; Stites & Harbison, PLLC

(57) ABSTRACT

A leg wear according to an embodiment of the present invention has a heel portion for covering a heel. In a plan view of a sole of the leg wear folded in a instep and sole planar shape, the length of a perpendicular line extending from a heel central point located at a center between a heel-side end of an outer gore line of the heel portion and a heel-side end of an inner gore line to an outer contour line is longer than the length of a perpendicular line extending from the heel central point to an inner contour line.

14 Claims, 11 Drawing Sheets

(56) References Cited

U.S. PATENT DOCUMENTS

| | | | |
|---|---|---|---|
| 2009/0276939 A1* | 11/2009 | Sho et al. | 2/239 |
| 2009/0282607 A1* | 11/2009 | Kaneda | A41B 11/02 2/239 |
| 2012/0102626 A1* | 5/2012 | Patel | 2/239 |
| 2012/0198601 A1* | 8/2012 | Shinga et al. | 2/239 |
| 2012/0266362 A1* | 10/2012 | Craig | 2/239 |
| 2014/0059742 A1* | 3/2014 | Patel | 2/239 |
| 2014/0338403 A1* | 11/2014 | Yoshimura | 66/177 |
| 2014/0345033 A1* | 11/2014 | Chang | 2/239 |
| 2015/0059059 A1* | 3/2015 | Teskey | 2/239 |

* cited by examiner

Fig.6
(a)
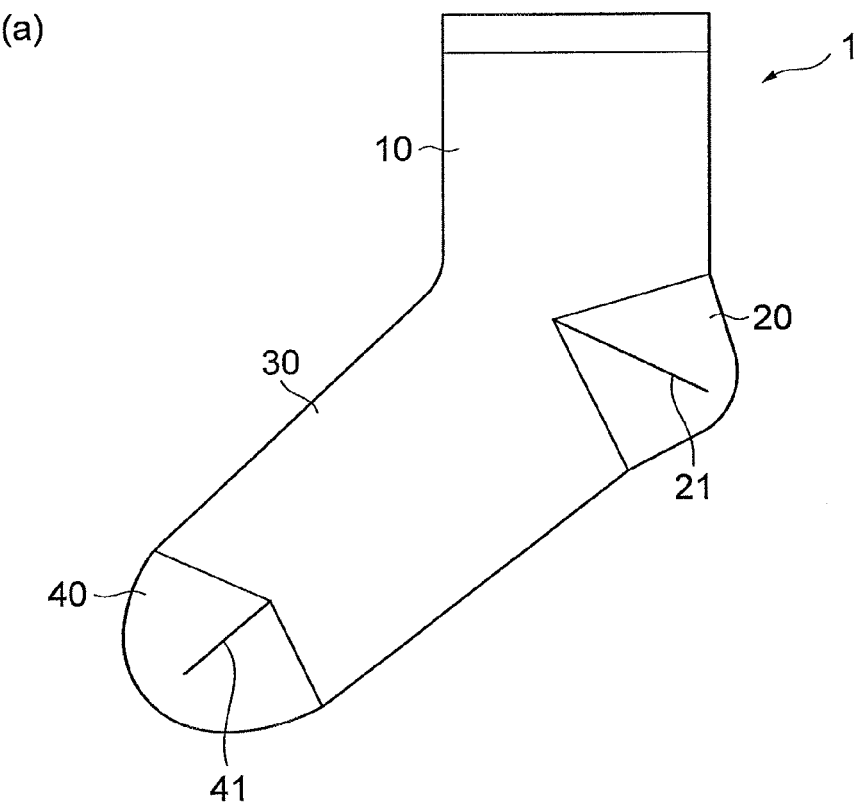
(b)
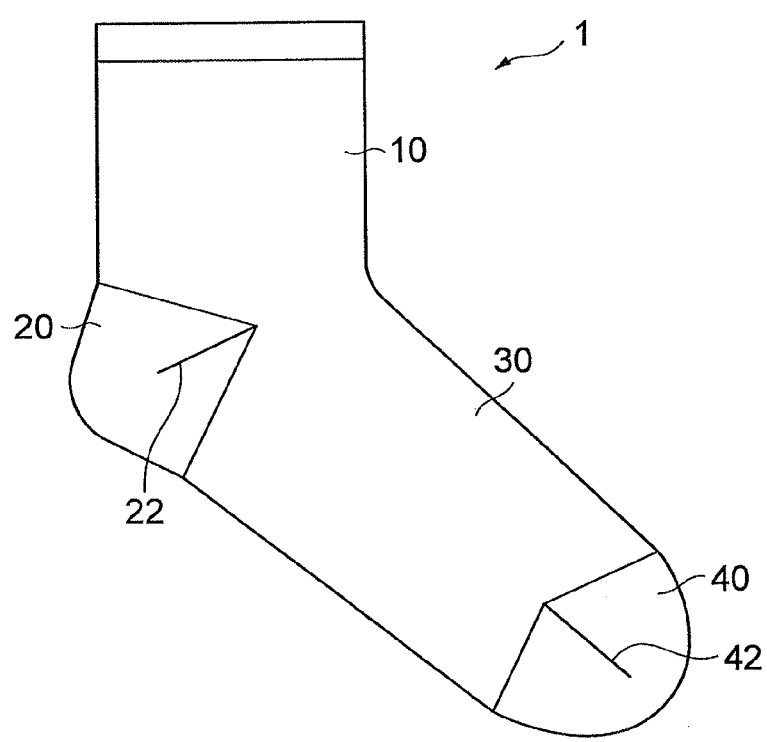

Fig.7
(a)
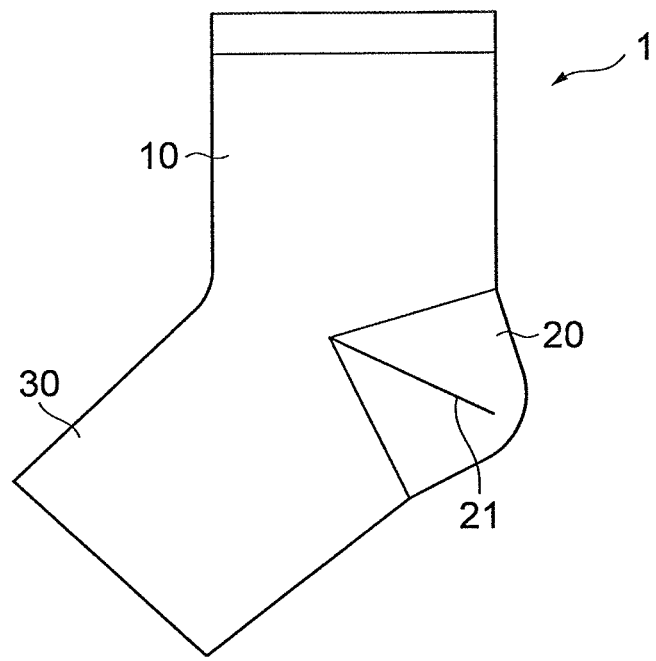
(b)
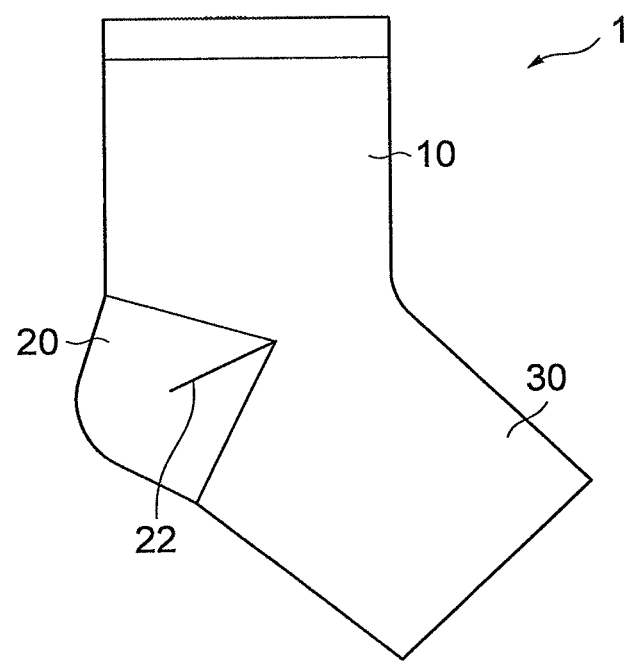

Fig.9
(a)  (b)
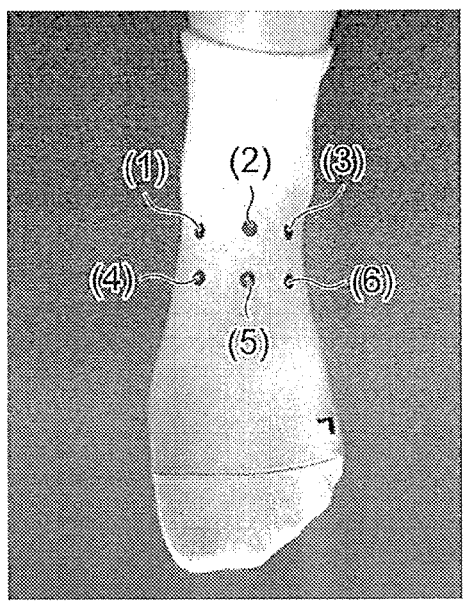
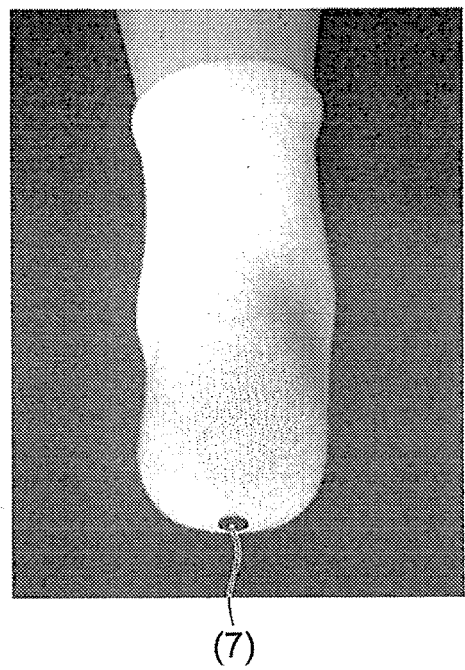

*Fig.11*
(a)
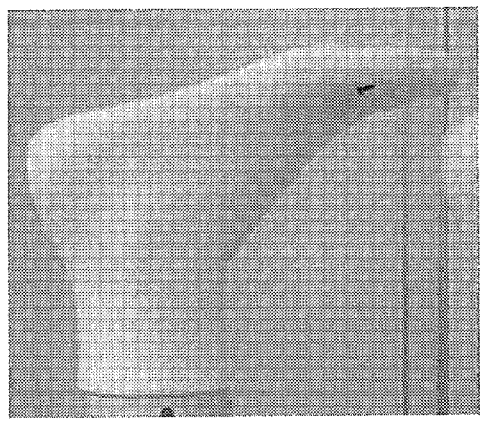
(b)
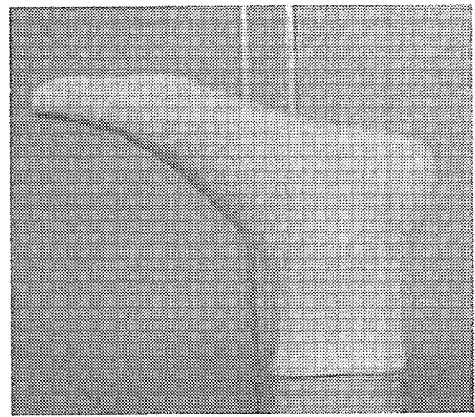
(c)
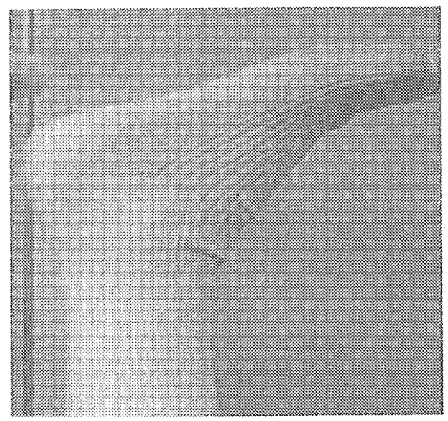
(d)
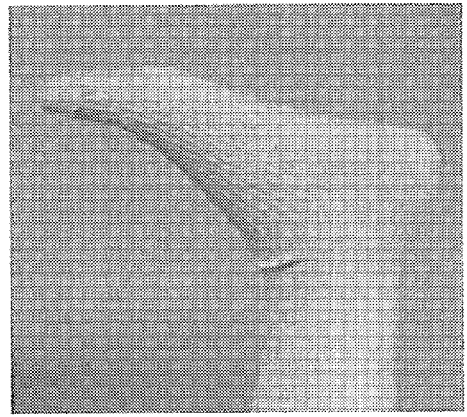

LEG WEAR

CROSS REFERENCE TO RELATED APPLICATION

This application claims the benefit of Japanese Patent Application No. 2013-135261 filed on Jun. 27, 2013, all of which are incorporated herein by reference in their entirety.

BACKGROUND OF THE INVENTION

1. Field of the Invention

The present invention relates to a leg wear.

2. Related Background Art

Japanese Patent No. 4147013, Japanese Utility Model Registration No. 3125430, and Japanese Patent No. 4590247 disclose socks as leg wear. Focusing attention on the fittability of its heel portion, each of the socks disclosed in Japanese Patent No. 4147013, Japanese Utility Model Registration No. 3125430, and Japanese Patent No. 4590247 is configured by forming the heel portion into asymmetry in view of the asymmetric shape of the heel of a wearer.

Japanese Patent No. 4147013 aims to improve foot comfort of the sock thereof, which can be worsened when the fabric on its heel portion becomes stretched and tightened as the wearer walks, due to the position of the heel bone leaning toward the external malleolus. Therefore, in this sock, the gore portion is formed on the outside of the heel portion. Japanese Patent No. 4147013 describes that the gore can be formed on the external malleolus side or internal malleolus side of the heel portion so that, when the sock is put on a certain type of foot and when walking, the gore can be positioned in an area applied with force of the heel portion. In other words, Japanese Patent No. 4147013 describes two inventions, a sock in which the gore is formed on the outside of the heel portion, and a sock in which the gore is formed on the inside of the heel portion, and it is considered that just one type of them is not enough to meet the needs of all wearers.

The sock disclosed in Japanese Utility Model Registration No. 3125430 aims to improve the fittability of its heel portion in careful consideration of the difference in shape of the heel portion. In this sock disclosed in Japanese Utility Model Registration No. 3125430, the heel portion is formed into asymmetry, in such a manner that the number and direction of branching gore lines on the inside are different from the number and direction of branching gore lines on the outside or in such a manner that the length of the gore lines is different on the inside and the outside. Note that Japanese Utility Model Registration No. 3125430 also describes that the gore lines on the inside and the gore lines on the outside may be switched. In other words, Japanese Utility Model Registration No. 3125430 also describes two inventions of socks, and it is considered that just one type of them is not enough to meet the needs of all wearers.

Japanese Patent No. 4590247 aims to provide a sock that conforms to the shape of a heel that is larger on the outside than it is on the inside, i.e., a sock that fits better on the heel, wherein the inside of the heel is made smaller than the outside by increasing the number of narrowing and widening steps, and the outside of the heel is made larger than the inside by increasing the number of wales toward the outside of the heel.

SUMMARY OF THE INVENTION

Incidentally, a sock needs to not only create fittability to the shape of its heel portion but also alleviate sagging (i.e., wrinkles) in its curved ankle portion on the instep side. Given this fact, increasing the tightness on the curved ankle portion on the instep side in order to alleviate sagging therein can lead to excessive circumferential (width directional) tightness on the heel portion on the sole side, deteriorating the wear comfort of the sock.

Thus, an object of the present invention is to provide a leg wear capable of achieving both alleviation of sagging (wrinkles) at a curved ankle portion on the instep side and reduction of tightness at a heel portion.

The inventors of the present application have found that both alleviation of sagging (wrinkles) at a curved ankle portion on the instep side and reduction of tightness at a heel portion (securing appropriate fittability) can be achieved by making the length A of a perpendicular line extending from a heel central point located at the center between a heel-side end of an outer gore line of the heel portion and a heel-side end of an inner gore line to an outer contour line, longer than the length B of a perpendicular line extending from the heel central point to an inner contour line, in a plan view of a sole of the leg wear folded in a instep and sole planar shape.

The leg wear of the present invention is a leg wear that has a heel portion for covering a heel, wherein, in a plan view of a sole of the leg wear folded in a instep and sole planar shape, a length A of a perpendicular line extending from a heel central point located at a center between a heel-side end of an outer gore line of the heel portion and a heel-side end of an inner gore line of the heel portion to an outer contour line is longer than a length B of a perpendicular line extending from the heel central point to an inner contour line.

According to this leg wear, in a plan view of a sole of the leg wear folded in a instep and sole planar shape, the length A of the perpendicular line extending from the heel central point located at the center between the heel-side end of the outer gore line of the heel portion and the heel-side end of the inner gore line to the outer contour line is longer than the length B of the perpendicular line extending from the heel central point to the inner contour line. Therefore, both alleviation of sagging (wrinkles) at a curved ankle portion on the instep side and reduction of tightness at the heel portion (securing appropriate fittability) can be achieved, improving the fit of the leg wear.

The inventors of the present application have also found that further alleviation of sagging (wrinkles) at the curved ankle portion on the instep side and further reduction of tightness at the heel portion (securing appropriate fittability) can be achieved by setting the ratio between the length A of the perpendicular line from the heel central point to the outer contour line and the length B of the perpendicular line from the heel central point to the inner contour line at approximately 6:4, in the plan view of the sole of the leg wear folded in the instep and sole planar shape.

In this leg wear, when a width W between the outer contour line and the inner contour line is assumed as 100% in the plan view of the sole of the leg wear folded in the instep and sole planar shape, the length A of the perpendicular line from the heel central point to the outer contour line may be 55% to 65%, and the length B of the perpendicular line from the heel central point to the inner contour line may be 45% to 35%.

According to this leg wear, when the width W between the outer contour line and the inner contour line is assumed as 100% in the plan view of the sole of the leg wear folded in the instep and sole planar shape, the length A of the perpendicular line from the heel central point to the outer contour line may be 55% to 65%, and the length B of the perpendicular line from the heel central point to the inner contour line may be 45% to 35%. Therefore, further alleviation of sagging (wrinkles) at the curved ankle portion on the instep side and further reduction of tightness at the heel portion (securing appropriate fittability) can be achieved, further improving the fit of the leg wear.

The length between the heel-side end and a lateral malleolus-side end of the outer gore line of the heel portion may be 1.212 times to 1.368 times the length between the heel-side end and a medial malleolus-side end of the inner gore line of the heel portion.

Further, a sole-side fabric width W1 and an instep-side fabric width W2 between the lateral malleolus-side end of the outer gore line of the heel portion and the medial malleolus-side end of the inner gore line of the heel portion may be 100%, respectively.

This configuration can set the ratio among the length on the outside of the heel portion, the length on the inside of the heel portion, and the length of the curved ankle portion on the instep side at an appropriate ratio, and therefore can achieve both further alleviation of sagging (wrinkles) at the curved ankle portion on the instep side and further reduction of tightness at the heel portion (securing appropriate fittability).

Moreover, the leg wear of the present invention may further have a toe portion for covering toes, wherein, in the plan view of the sole of the leg wear folded in a instep and sole planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the inner contour line.

According to this configuration, the length C of the perpendicular line extending from the toe central point located at the center between the toe-side end of the outer gore line of the toe portion and the toe-side end of the inner gore line to the outer contour line is longer than the length D of the perpendicular line extending from the toe central point to the inner contour line. Therefore, fittability to the shape of the toe portion can be improved.

In this leg wear, when a width W between the outer contour line and the inner contour line is assumed as 100% in the plan view of the sole of the leg wear folded in the instep and sole planar shape, the length C of the perpendicular line from the toe central point to the outer contour line may be 55% to 65%, and the length D of the perpendicular line from the toe central point to the inner contour line may be 45% to 35%.

According to this configuration, the ratio between the length C of the perpendicular line from the toe central point to the outer contour line and the length D of the perpendicular line from the toe central point to the inner contour line is approximately 6:4, improving fittability to the shape of the toe portion.

The length between the toe-side end and an outer end of the outer gore line of the toe portion may be 1.212 times to 1.368 times the length between the toe-side end and an inner end of the inner gore line of the toe portion.

The length between the heel portion and the toe portion may be increased in accordance with a difference between the length A of the perpendicular line from the heel central point to the outer contour line and the length B of the perpendicular line from the heel central point to the inner contour line, and a difference between the length C of the perpendicular line from the toe central point to the outer contour line and the length D of the perpendicular line from the toe central point to the inner contour line.

The inventors of the present invention have found that a sense of tightness is felt between the toes and the heel in the longitudinal direction when differentiating the length A of the perpendicular line extending from the heel central point to the outer contour line from the length B of the perpendicular line extending from the heel central point to the inner contour line, or when differentiating the length C of the perpendicular line extending from the toe central point to the outer contour line from the length D of the perpendicular line extending from the toe central point to the inner contour line. However, because the length between the heel portion and the toe portion is increased in accordance with the difference between the length A of the perpendicular line from the heel central point to the outer contour line and the length B of the perpendicular line from the heel central point to the inner contour line, and the difference between the length C of the perpendicular line from the toe central point to the outer contour line and the length D of the perpendicular line from the toe central point to the inner contour line, the sense of tightness felt between the toes and the heel in the longitudinal direction can be alleviated, improving the wear comfort of the leg wear.

The present invention is capable of not only accomplishing both alleviation of sagging (wrinkles) at the curved ankle portion on the instep side and reduction of tightness at the heel portion, but also improving the wear comfort of the leg wear.

(a) and (b) of FIG. 6 are an external plan view and an internal plan view, respectively, of a sock (left foot) according to a modification of the present invention, the sock being folded in a horizontal planar shape.

(a) and (b) of FIG. 7 are an external plan view and an internal plan view, respectively, of a sock (left foot) according to another modification of the present invention, the sock being folded in a horizontal planar shape.

Figure 8:
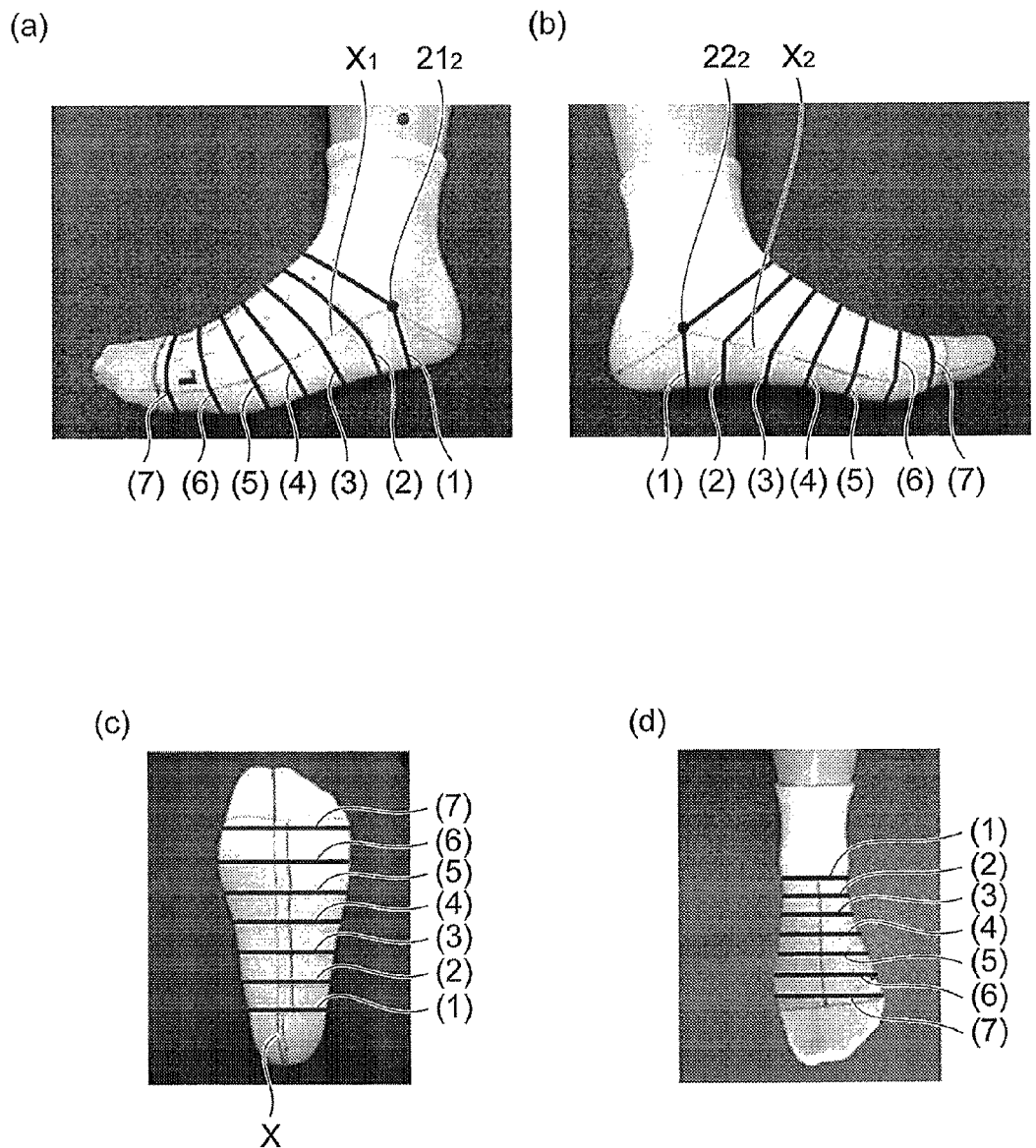

(a) to (d) of FIG. 8 are diagrams each showing measured sections obtained in Evaluation 1.

(a) and (b) of FIG. 9 are diagrams each showing measured sections obtained in Evaluation 2.

Figure 10:
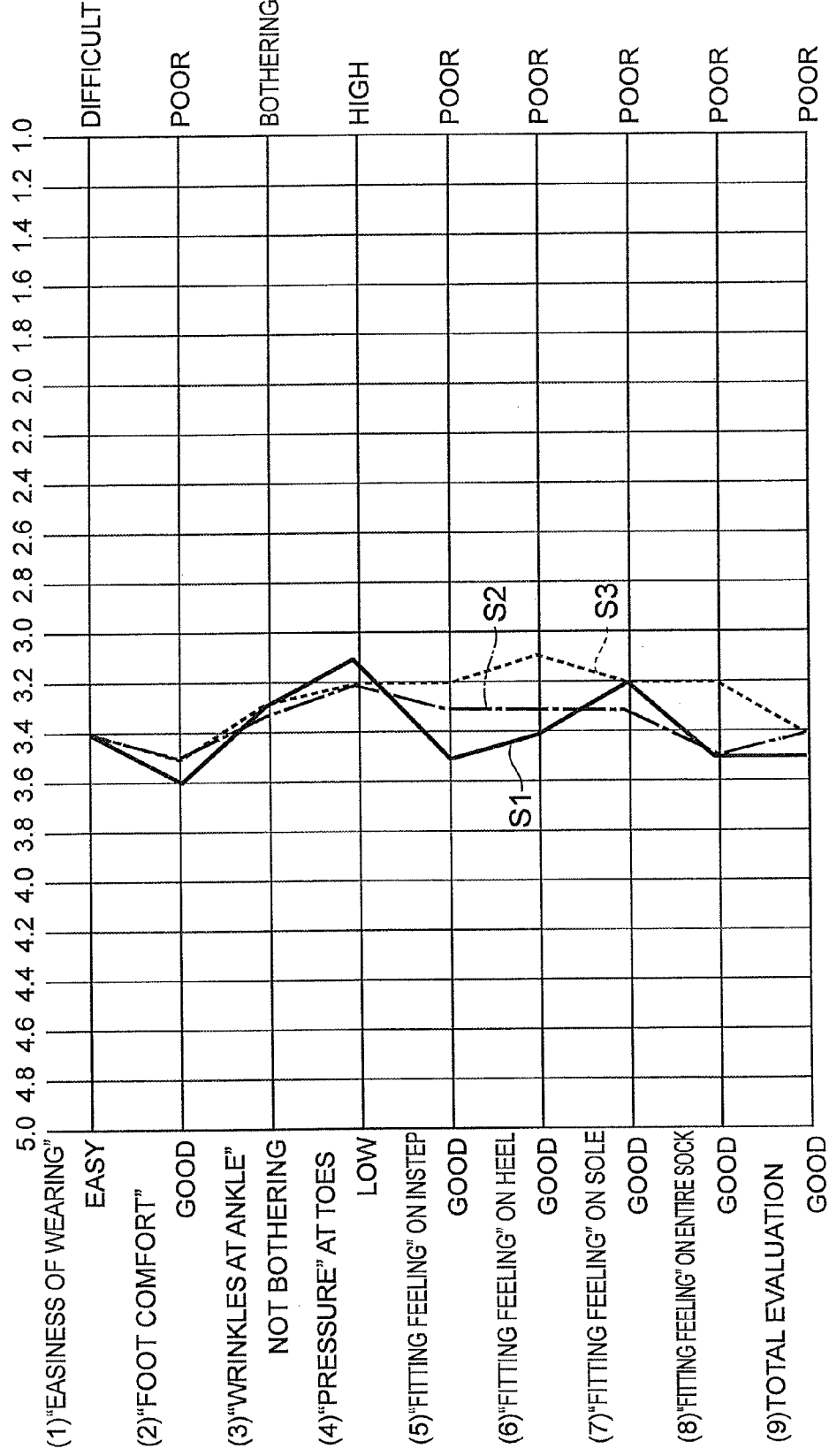

FIG. 10 is a diagram showing the results of Evaluation 3.

(a) to (d) of FIG. 11 are images of the outside and inside of a sock of Example 1 and of a conventional sock, which are put on lasts.

DESCRIPTION OF THE PREFERRED EMBODIMENTS

A preferred embodiment of the present invention is described hereinafter in detail with reference to the drawings. The same reference numerals/characters are used for indicating the same or like portions throughout the drawings.

Figure 1:
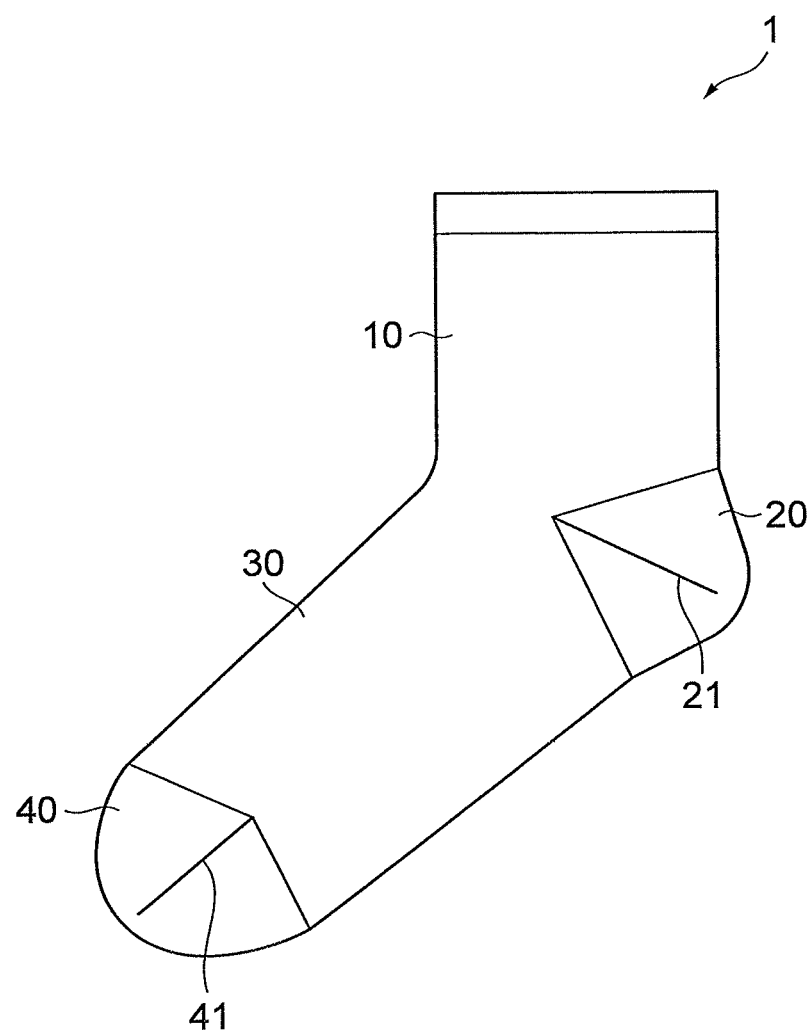
FIG. 1 is an external plan view of a sock (left foot) according to an embodiment of the present invention, the sock being folded in a horizontal planar shape.
Figure 2:
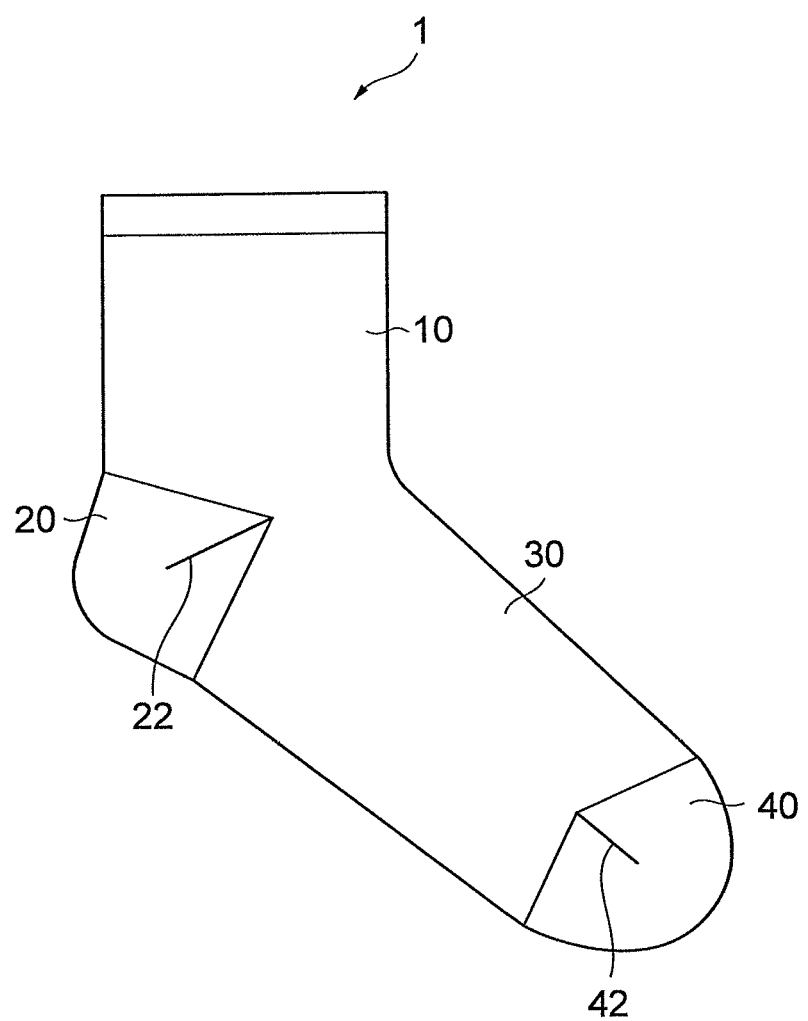
FIG. 2 is an internal plan view of the sock (left foot) according to the embodiment of the present invention, the sock being folded in a horizontal planar shape.
Figure 3:
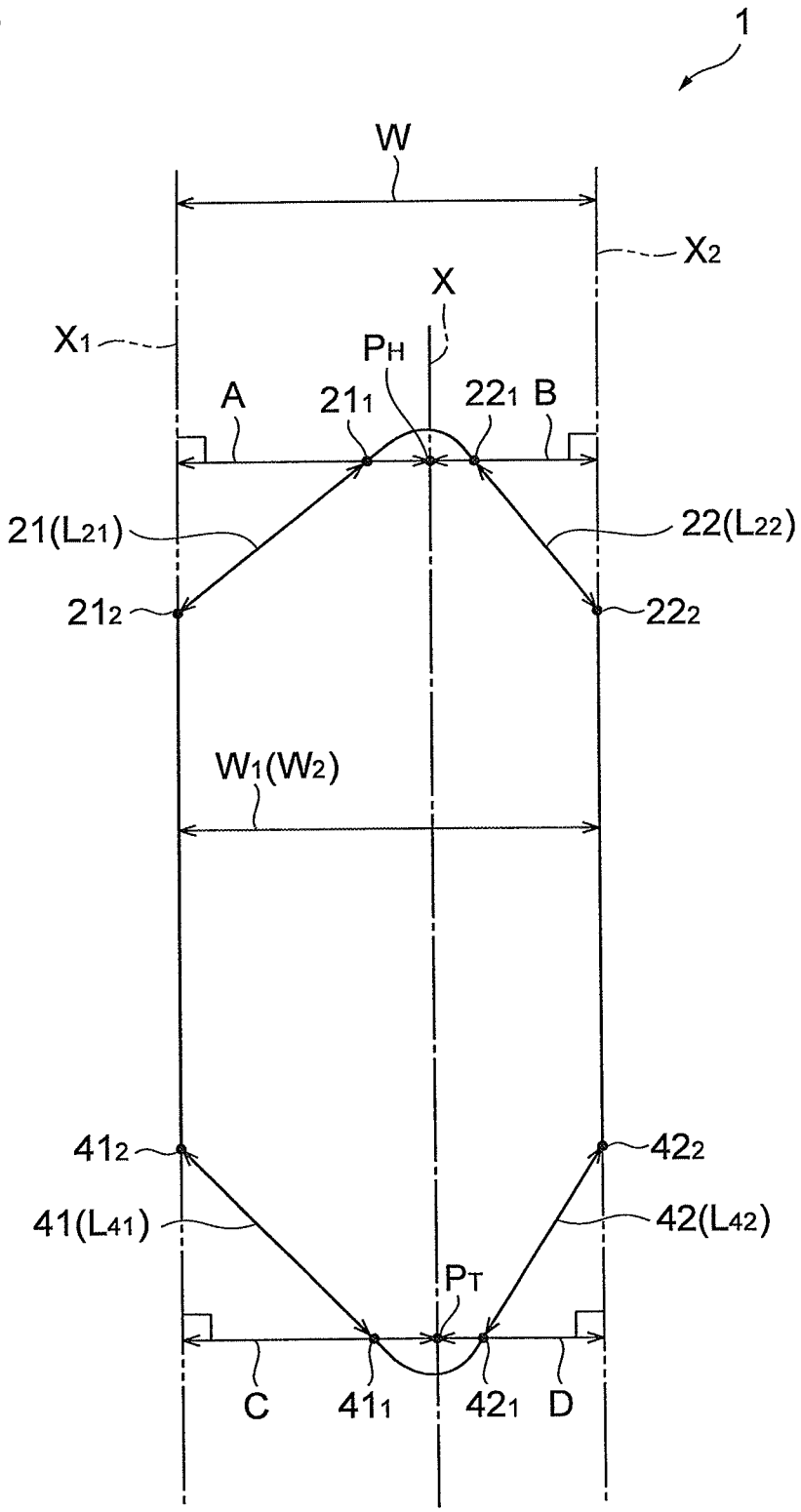
FIG. 3 is a plan view of a sole of the sock (left foot) according to the embodiment of the present invention, the sock being folded in a instep and sole planar shape.
Figure 4:
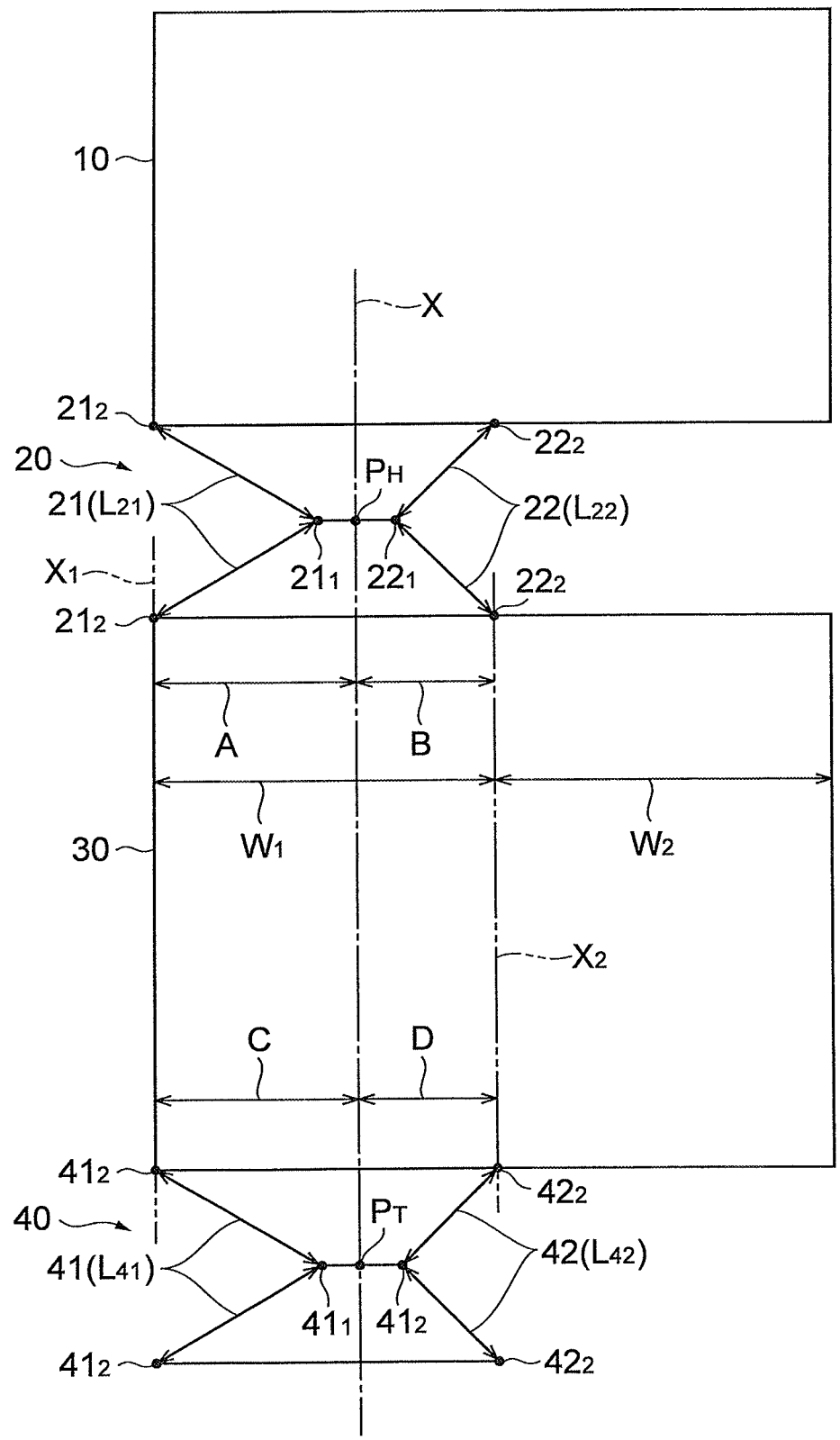
FIG. 4 is a development diagram of the sock shown in FIGS. 1 to 3.
Figure 5:
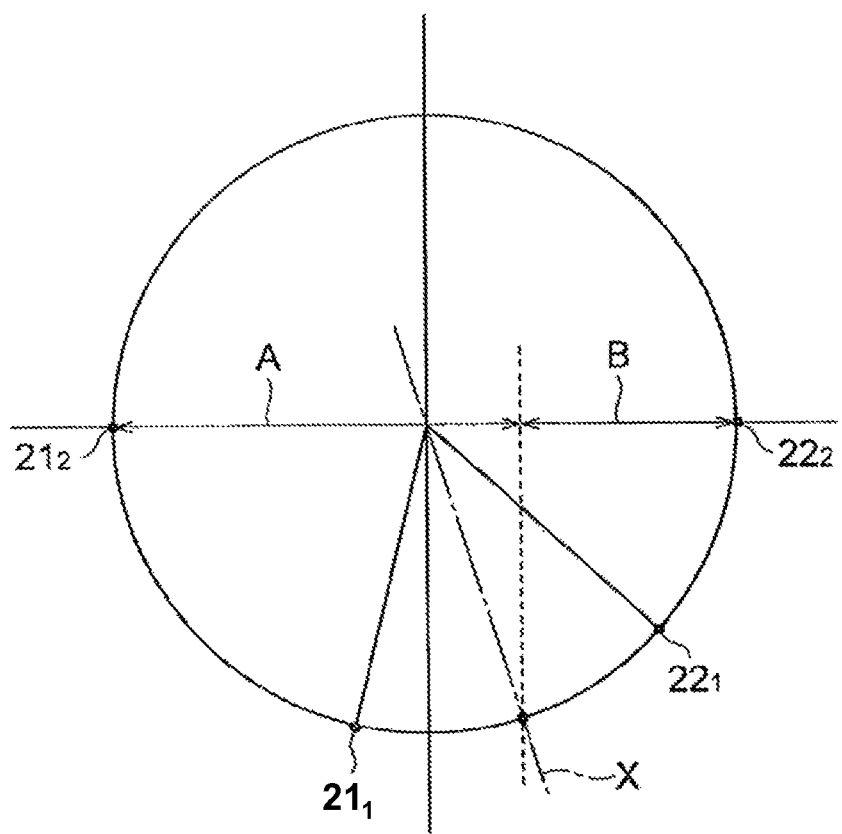
FIG. 5 is a diagram showing a method for forming a heel portion of the sock shown in FIGS. 1 to 3.

FIG. 1 is an external plan view of a sock (left foot) according to an embodiment of the present invention, the sock being folded in a horizontal planar shape. FIG. 2 is an internal plan view of the sock (left foot) according to the embodiment of the present invention, the sock being folded in a horizontal planar shape. FIG. 3 is a plan view of a sole of the sock (left foot) according to the embodiment of the present invention, the sock being folded in a instep and sole planar shape. FIG. 4 is a development diagram of the sock shown in FIGS. 1 to 3. FIG. 5 is a diagram showing a method for forming a heel portion of the sock shown in FIGS. 1 to 3.

A sock 1 shown in FIGS. 1 to 3 is configured by sequentially forming a tubular portion 10 covering an area above the ankle, a heel portion 20 covering the heel, a tubular portion 30 covering the sole and instep, and a toe portion 40 covering the toes. For example, this type of sock is formed using a circular knitting machine.

The circular knitting machine used is a fully computerized knitting machine with a cylinder. This fully computerized system is a knitting system that can execute a series of designing and knitting where an electromagnetic recording medium is used to transfer the design data on stitches of the whole product, which are created on a computer, and then the product is electrically and automatically knitted based on the design data on stitches.

This type of circular knitting machine forms a yarn into a loop by rotating its cylinder and repeatedly moving the circumferentially disposed needles up and down (e.g., plain stitch.). One course is knitted by a 360-degree rotation (one rotation), and repetition of such knitting by rotating the cylinder in the same direction leads to the formation of the tubular portions 10, 30. Counterclockwise rotation of the cylinder is generally called "positive rotation," and clockwise rotation "negative rotation."

The heel portion 20 and the toe portion 40, on the other hand, are formed using any of the needles by repeating the positive rotation and negative rotation of the cylinder, course by course. This motion of the cylinder is generally called "reciprocal rotation." Needle-up (referred to as "narrowing," hereinafter) is carried out to form a half of the heel portion 20, and needle-down (referred to as "widening," hereinafter) is carried out to form the remaining half of the heel portion 20. Gore lines 21, 22 are join lines between the narrowing section and the widening section in the heel portion 20. Similarly, needle-up (referred to as "narrowing," hereinafter) is carried out to form a half of the toe portion 40, and needle-down (referred to as "widening," hereinafter) is carried out to form the remaining half of the toe portion 40. Gore lines 41, 42 are join lines between the narrowing section and the widening section in the toe portion 40 (see FIGS. 4 and 5, for example).

In the present embodiment, the length A of a perpendicular line extending from a heel central point $P_H$ located at the center between a heel-side end $21_1$ of the outer gore line 21 of the heel portion 20 and a heel-side end $22_1$ of the inner gore line 22 to an outer contour line $X_1$ can be made longer than the length B of a perpendicular line extending from the heel central point $P_H$ to an inner contour line $X_2$, by making the number of narrowing stitches and the number of widening stitches on the lateral malleolus side of the heel portion 20 greater than the number of narrowing stitches and the number of widening stitches on the medial malleolus side of the heel portion 20.

Specifically, in the plan views of the sole of the sock folded in a instep and sole planar shape as shown in FIGS. 3 to 5, when the width W between the outer contour line $X_1$ and the inner contour line $X_2$ is assumed as 100%, the length A of the perpendicular line extending from the heel central point $P_H$ located at the center between the heel-side end $21_1$ of the outer gore line 21 of the heel portion 20 and the heel-side end $22_1$ of the inner gore line 22 to the outer contour line $X_1$ is 55% to 65%, while the length B of the perpendicular line extending from the heel central point $P_H$ to the inner contour line $X_2$ is 45% to 35%. Preferably, the ratio between A and B is 6:4.

The length $L_{21}$ between the heel-side end $21_1$ and a lateral malleolus-side end $21_2$ of the outer gore line 21 of the heel portion 20 is 1.212 times to 1.368 times the length $L_{22}$ between the heel-side end $22_1$ and a medial malleolus-side end $22_2$ of the inner gore line 22. It is preferred that the length $L_{21}$ be 1.222 times the length $L_{22}$. In case of an adult male, for example, it is preferred that the length $L_{21}$ be approximately 5.5 cm and the length $L_{22}$ be approximately 4.5 cm. The length $L_{21}$ can be set at approximately 5.7 cm and the length $L_{22}$ at approximately 4.7 cm by increasing the number of courses of the heel portion. The length $L_{21}$ can be set at approximately 5.2 cm and the length $L_{22}$ at approximately 3.8 cm by reducing the number of courses in the heel portion. In this manner, the outer part of the heel portion, which could be excessively tight, can be made more relaxed, and as a result the tightness that can be felt at the entire heel portion can be alleviated.

Furthermore, when the width W between the outer contour line $X_1$ and the inner contour line $X_2$ is assumed as 100%, a sole-side fabric width W1 and an instep-side fabric width W2 between the lateral malleolus-side end $21_2$ of the outer gore line 21 of the heel portion 20 and the medial malleolus-side end $22_2$ of the inner gore line 22 are 100%, respectively.

Similarly, in the present embodiment, the length C of a perpendicular line extending from a toe central point $P_T$ located at the center between a toe-side end $41_1$ of the outer gore line 41 of the toe portion 40 and a toe-side end $42_1$ of the inner gore line 42 to the outer contour line $X_1$ can be made longer than the length D of a perpendicular line extending from the toe central point $P_T$ to the inner contour line $X_2$, by making the number of narrowing stitches and the number of widening stitches on the outside of the toe portion 40 greater than the number of narrowing stitches and the number of widening stitches on the inside of the toe portion 40.

Specifically, in the plan views of the sole of the sock folded in a instep and sole planar shape, when the width W between the outer contour line $X_1$ and the inner contour line $X_2$ is assumed as 100%, the length C of the perpendicular line extending from the toe central point $P_T$ located at the center between the toe-side end $41_1$ of the outer gore line 41 of the toe portion 40 and the toe-side end $42_1$ of the inner gore line 42 to the outer contour line $X_1$ is 55% to 65%, while the length D of the perpendicular line extending from the toe central point $P_T$ to the inner contour line $X_2$ is 45% to 35%. Preferably, the ratio between C and D is 6:4. According to such a configuration, the toe portion and the heel portion can counterbalance each other, preventing an unwanted migration of the sock.

The length $L_{41}$ between the toe-side end $41_1$ and an outer end $41_2$ of the outer gore line 41 of the toe portion 40 is 1.212 times to 1.368 times the length $L_{42}$ between the toe-side end $42_1$ and an inner end $42_2$ of the inner gore line 42. It is preferred that the length $L_{41}$ be 1.222 times the length $L_{42}$. Such a configuration can prevent sagging of the sock at a curved ankle portion on the instep side, which is caused due to sagging at the toe portion, and unwanted migration at the heel portion.

Furthermore, in the present embodiment the length of the tubular portion 30 between the heel portion 20 and the toe portion 40 is increased in accordance with the difference between the length A of the perpendicular line from the heel central point $P_H$ to the outer contour line $X_1$ and the length B of the perpendicular line from the heel central point $P_H$ to the inner contour line $X_2$, and the difference between the length C of the perpendicular line from the toe central point $P_T$ to the outer contour line $X_1$ and the length D of the perpendicular line from the toe central point $P_T$ to the inner contour line $X_2$.

In case of an adult male, for example, increasing the number of courses by twenty can obtain the length of the tubular portion one size larger than a designed size.

When the sock 1 of the present embodiment is put on, the lateral malleolus-side end of the outer gore line of the heel portion is positioned above the level of the medial malleolus-side end of the inner gore line of the heel portion.

The inventors of the present application, therefore, have found that not only is it possible to improve fittability of the sock to the shape of the heel portion, but also alleviation of sagging (wrinkles) at the curved ankle portion on the instep side and reduction of the tightness at the heel portion (securing appropriate fittability) can be achieved by setting the ratio between the length A of the perpendicular line extending from the heel central point $P_H$ located at the center between the heel-side end $21_1$ of the outer gore line 21 of the heel portion 20 and the heel-side end $22_1$ of the inner gore line 22 to the outer contour line $X_1$, and the length B of the perpendicular line extending from the heel central point $P_H$ to an inner contour line $X_2$, to be approximately 6:4, in the plan views of the sole of the sock folded in a instep and sole planar shape.

According to the sock 1 of the present embodiment, in the plan views of the sole of the sock folded in a instep and sole planar shape, when the width W between the outer contour line $X_1$ and the inner contour line $X_2$ is assumed as 100%, the length A of the perpendicular line extending from the heel central point $P_H$ located at the center between the heel-side end $21_1$ of the outer gore line 21 of the heel portion 20 and the heel-side end $22_1$ of the inner gore line 22 to the outer contour line $X_1$ is 55% to 65%, while the length B of the perpendicular line extending from the heel central point $P_H$ to the inner contour line $X_2$ is 45% to 35%. This can not only improve fittability of the sock to the shape of the heel portion, but also achieve both alleviation of sagging (wrinkles) at the curved ankle portion on the instep side and reduction of the tightness at the heel portion (securing appropriate fittability), and as a result wear comfort of the sock can be improved.

According to the sock 1 of the present embodiment, when the width W between the outer contour line $X_1$ and the inner contour line $X_2$ is assumed as 100%, the sole-side fabric width W1 and the instep-side fabric width W2 between the lateral malleolus-side end $21_2$ of the outer gore line 21 of the heel portion 20 and the medial malleolus-side end $22_2$ of the inner gore line 22 are 100%, respectively. Hence, the ratio among the length of the heel portion 20 on the outside, the length of the heel portion 20 on the inside, and the length of the curved ankle portion on the instep side can appropriately be set, further improving fittability of the sock to the shape of the heel portion and achieving both alleviation of sagging (wrinkles) at the curved ankle portion on the instep side and reduction of the tightness at the heel portion.

According to the sock 1 of the present embodiment, fittability of the sock to the shape of the toe portion can be improved by setting the ratio between the length C of the perpendicular line extending from the toe central point $P_T$ located at the center between the toe-side end $41_1$ of the outer gore line 41 of the toe portion 40 and the toe-side end $42_1$ of the inner gore line 42 to the outer contour line $X_1$ and the length D of the perpendicular line extending from the toe central point $P_T$ to the inner contour line $X_2$, to be approximately 6:4.

Incidentally, the inventors of the present application have found that a sense of tightness is felt between the toes and the heel in the longitudinal direction when differentiating the length A of the perpendicular line extending from the heel central point $P_H$ to the outer contour line $X_1$ from the length B of the perpendicular line extending from the heel central point $P_H$ to the inner contour line $X_2$, or when differentiating the length C of the perpendicular line extending from the toe central point $P_T$ to the outer contour line $X_1$ from the length D of the perpendicular line extending from the toe central point $P_T$ to the inner contour line $X_2$.

In this regard, according to the sock 1 of the present embodiment, the length of the tubular portion 30 between the heel portion 20 and the toe portion 40 is increased in accordance with the difference between the length of the outer gore line 21 of the heel portion 20 and the length of the inner gore line 22 of the heel portion 20, and the difference between the length of the outer gore line 41 of the toe portion 40 and the length of the inner gore line 42 of the toe portion 40. Thus, the sense of tightness felt between the toes and the heel in the longitudinal direction can be alleviated, improving the wear comfort of the sock.

Note that the present invention is not limited to the embodiment described above, and various modifications can be made to the present invention. For example, in the present embodiment, the ratio between the length A of the perpendicular line extending from the heel central point $P_H$ of the heel portion 20 to the outer contour line $X_1$ and the length B of the perpendicular line extending from the heel central point $P_H$ to the inner contour line $X_2$ is set at approximately 6:4. However, the ratio between A and B is not limited thereto and may take any ratio as long as the values of A and B are different from each other.

Similarly, in the present embodiment, the ratio between the length C of the perpendicular line extending from the toe central point $P_T$ of the toe portion 40 to the outer contour line $X_1$ and the length D of the perpendicular line extending from the toe central point $P_T$ to the inner contour line $X_2$ is set at approximately 6:4. However, the ratio between C and D is not limited thereto and may take any ratio as long as the values of C and D are different from each other.

In addition, the present invention is characterized in that the length A of the perpendicular line extending from the heel central point $P_H$ of the heel portion 20 to the outer contour line $X_1$ is made longer than the length B of the perpendicular line extending from the heel central point $P_H$ to the inner contour line $X_2$, and, as shown in FIG. 6, the ratio between the length C of the perpendicular line extending from the toe central point $P_T$ of the toe portion 40 to the outer contour line $X_1$ and the length D of the perpendicular line extending from the toe central point $P_T$ to the inner contour line $X_2$ may be 1:1, as with the prior art.

The present embodiment has illustrated a sock, but the characteristics of the present invention may be applied to a heel portion of a tubular leg wear that does not have a toe portion (e.g., medical or athletic leg wear), as shown in FIG. 7.

The present embodiment has also illustrated a leg wear that is formed by a knitting method using a circular knitting machine, but the characteristics of the present invention can be applied to a leg wear formed by another knitting method. The characteristics of the present invention can also be applied to a leg wear that is formed by cutting out a fabric into a plurality of pieces and sewing these pieces together. In this type of leg wear, the join lines located where the gore lines are in the sock of the present embodiment are referred to as gore lines of the present invention.

Examples

Examples 1 to 3 of the sock 1 of the present embodiment shown in FIGS. 1 to 3 were created, and the following evaluations 1 to 3 were carried out on these examples. These evaluations compared Examples 1 to 3 with the prior art.

Examples 1 to 3 each were formed by using a 32-denier single yarn as a face yarn and using an elastic yarn with a 75-denier polyester yarn wound around a 30-denier polyurethane yarn as a back yarn (FTY 30/75). Examples 1 to 3 are common in terms of that the length A from the heel central point $P_H$ of the heel portion 20 to the outer contour line $X_1$ and the length C from the toe central point $P_T$ to the outer contour line $X_1$ are within the range of 55% to 65% and that the length B from the heel central point $P_H$ to the inner contour line $X_2$ and the length D from the toe central point $P_T$ to the inner contour line $X_2$ are within the range of 45% to 35%. However, Examples 1 to 3 are different from one another in terms of the followings.

In Example 1, the length $L_{21}$ of the outer gore line 21 of the heel portion 20 was 5.5 cm and the length $L_{22}$ of the inner gore line 22 was 4.5 cm. In other words, the length $L_{21}$ of the outer gore line 21 was approximately 1.222 times the length $L_{22}$ of the inner gore line 22.

In Example 2, the length $L_{21}$ of the outer gore line 21 was 5.7 cm and the length $L_{22}$ of the inner gore line 22 was 4.7 cm because the heel portion 20 had two more courses than that of Example 1. In other words, the length $L_{21}$ of the outer gore line 21 was approximately 1.212 times the length $L_{22}$ of the inner gore line 22.

In Example 3, the length $L_{21}$ of the outer gore line 21 was 5.2 cm and the length $L_{22}$ of the inner gore line 22 was 3.8 cm because the heel portion 20 had two less courses than that of Example 1. In other words, the length $L_{21}$ of the outer gore line 21 was approximately 1.368 times the length $L_{22}$ of the inner gore line 22.

The prior art, on the other hand, is different from these examples mainly in that the ratio between the length A from the heel central point of the heel portion to the outer contour line and the length B from the heel central point to the inner contour line is 1:1 and that the ratio between the length C from the toe central point of the toe portion to the outer contour line and the length D from the toe central point to the inner contour line is 1:1.

[Evaluation 1]

In Evaluation 1, Example 1 and the prior art were put on lasts, and circumferential (width directional) elongation percentages of the sections were measured. The measurement environment was established by setting up the temperature and humidity of a constant temperature and humidity room at 20° C. and 65% RH respectively. In each of the examples, Example 1 and the prior art, the tubular portion 30 between the heel portion 20 and the toe portion 40 was sectioned into approximately seven parts in the longitudinal direction, as shown in FIG. 8. The circumferences of these seven parts were the measured sections. Further, each of the circumferences was divided into two sections, an instep section and a sole section, by the outer contour line $X_1$ and the inner contour line $X_2$, and then the instep section and the sole section were divided into two sections to obtain an instep outer section, an instep inner section, a sole outer section, and a sole inner section. Therefore, the seven circumferences×these four sections were measured. A line was drawn on the seven circumferences by using a permanent marker, and then the length of the line was measured before and after each of the socks of Example 1 and the prior art were put on the lasts, to compute the elongation percentage of each sock on the last with respect to the elongation percentage of the same that was not yet put on the last. The results of these measurements and computation are shown in Table 1.

TABLE 1

| | | Prior art | | | Example 1 | | |
|---|---|---|---|---|---|---|---|
| | | Before put on last (mm) | After put on last (mm) | Elongation percentage (%) | Before put on last (mm) | After put on last (mm) | Elongation percentage (%) |
| Outside of instep | (1) | 49 | 81 | 165 | 48 | 82 | 171 |
| | (2) | 44 | 76 | 173 | 44 | 75 | 170 |
| | (3) | 44 | 68 | 155 | 44 | 73 | 166 |
| | (4) | 44 | 66 | 150 | 43 | 66 | 153 |
| | (5) | 44 | 64 | 145 | 44 | 64 | 145 |
| | (6) | 44 | 61 | 139 | 44 | 60 | 136 |
| | (7) | 46 | 58 | 126 | 45 | 59 | 131 |
| Inside of instep | (1) | 49 | 87 | 178 | 49 | 93 | 190 |
| | (2) | 43 | 78 | 181 | 44 | 81 | 184 |
| | (3) | 43 | 73 | 170 | 43 | 73 | 170 |
| | (4) | 43 | 66 | 153 | 42 | 68 | 162 |
| | (5) | 43 | 64 | 149 | 43 | 65 | 151 |
| | (6) | 43 | 63 | 147 | 45 | 65 | 144 |
| | (7) | 44 | 58 | 132 | 44 | 57 | 130 |
| Outside of sole | (1) | 44 | 74 | 168 | 44 | 63 | 143 |
| | (2) | 42 | 65 | 155 | 42 | 61 | 145 |
| | (3) | 42 | 60 | 143 | 41 | 56 | 137 |
| | (4) | 43 | 58 | 135 | 43 | 56 | 130 |
| | (5) | 45 | 60 | 133 | 43 | 58 | 135 |
| | (6) | 46 | 62 | 135 | 44 | 60 | 136 |
| | (7) | 45 | 61 | 136 | 44 | 56 | 127 |
| Inside of sole | (1) | 44 | 71 | 161 | 44 | 65 | 148 |
| | (2) | 40 | 63 | 158 | 40 | 60 | 150 |
| | (3) | 40 | 56 | 140 | 39 | 55 | 141 |
| | (4) | 41 | 55 | 134 | 39 | 54 | 138 |
| | (5) | 42 | 56 | 133 | 41 | 57 | 139 |
| | (6) | 43 | 61 | 142 | 42 | 60 | 143 |
| | (7) | 43 | 61 | 142 | 44 | 49 | 111 |

Looking at the circumferences (1) to (3) in the instep outer section and the circumferences (1) to (4) in the instep inner section (in the vicinity of the curved ankle portion on the instep side) of each example shown in Table 1, the elongation percentage of Example 1 is higher than that of the prior art. This indicates that the tension acting in the width direction has reduced the level of sagging (i.e., wrinkles) in the curved ankle portion on the instep side. Looking at the circumferences (1) and (2) in the sole outer section and the circumferences (1) and (2) in the sole inner section (in the vicinity of the heel portion) of each example, on the other hand, the elongation percentage of Example 1 is lower than that of the prior art, which indicates that the tightness at the heel portion was alleviated.

[Evaluation 2]

In Evaluation 2, Example 1 and the prior art were put on lasts, and compression of each section was measured. The measurement environment was established by setting up the temperature and humidity of a constant temperature and humidity room at 20° C. and 65% RH respectively. In each of the examples, Example 1 and the prior art, seven sections shown in FIG. 9 were measured: (1) an upper inner part of the curved ankle portion on the instep side, (2) an upper central part of the curved ankle portion on the instep side, (3) an upper outer part of the curved ankle portion on the instep side, (4) a lower inner part of the curved ankle portion on the instep side, (5) a lower central part of the curved ankle portion on the instep side, (6) a lower outer part of the curved ankle portion on the instep side, and (7) a heel portion. Air pack contact pressure measuring devices A0101-G (AMI Techno CO., LTD.) and MSX-20M, an average last designed for Japanese men in their 20s (NANASAI CO., LTD.), were used for the measurement. Specifically, the air packs were attached to the measured sections of Example 1 or of the prior art which was then put on the last. The measured values obtained one minute after the measurement were recorded. Each of these measured sections was measured three times. The average value of each of the measured sections of Example 1 and the prior art is shown in Table 2.

TABLE 2

|  | Prior art (hPa) | Example 1 (hPa) |
|---|---|---|
| (1) Upper inner part of the curved ankle portion on the instep side | 12.3 | 12.3 |
| (2) Upper central part of the curved ankle portion on the instep side | 10.0 | 10.3 |
| (3) Upper outer part of the curved ankle portion on the instep side | 15.0 | 14.7 |
| (4) Lower inner part of the curved ankle portion on the instep side | 16.0 | 15.7 |
| (5) Lower central part of the curved ankle portion on the instep side | 20.7 | 19.3 |
| (6) Lower outer part of the curved ankle portion on the instep side | 14.7 | 14.0 |
| (7) Heel portion | 40.7 | 38.0 |

Looking at (5) the lower central part of the curved ankle portion on the instep side, (6) the lower outer part of the curved ankle portion on the instep side, and (7) the heel portion of each example shown in Table 2, the compression of Example 1 is lower than that of the prior art. This indicates that the level of sagging (wrinkles) in the curved ankle portion on the instep side has been reduced as described above, and at the same time the tightness at the curved ankle portion on the instep side and at the heel portion has been reduced.

[Evaluation 3]

In Evaluation 3, Examples 1 to 3 and the prior art were put on lasts, and ten adult male monitors were asked about the fitting feeling. The evaluation environment was established by setting up the temperature and humidity of a constant temperature and humidity room at 20° C. and 65% RH respectively. The evaluation results are shown in FIG. 10. In FIG. 10, with the fit of the prior art assumed as 3.0, the fit of Example 1 is shown in a curve S1, the fit of Example 2 in a curve S2, and the fit of Example 3 in S3.

FIG. 10 shows that all of the items provided better fit in Examples 1 to 3 than the prior art. Moreover, out of Examples 1 to 3, Example 1 provided good fit overall, especially at the instep portion and the heel portion.

(a) of FIG. 11 shows an image of the outside of Example 1 on a last. (b) of FIG. 11 shows an image of the inside of Example 1 on the last. (c) of FIG. 11 shows an image of the outside of the prior art on a last. (d) of FIG. 11 shows an image of the inside of the prior art on the last. FIG. 11 shows that Example 1 can reduce sagging (i.e., wrinkles) of the curved ankle portion on the instep side, unlike the prior art.

The observations by the inventors of the present application based on these evaluation results are as follows. Compared to the inside of a foot, the outside of the foot has less of a curve such as the arch and hence a larger volume and therefore requires a larger amount of fabric in order to create more space for providing an appropriate level of fit. However, an excessive amount of fabric can create sagging and wrinkles, significantly worsening the fit of the sock.

Also, the vicinity of the section on the outside of the foot that comes into contact with the ground has a wide angle (an angle as wide as a right angle). This part of the foot grabs the ground by deforming the skin and underlying tissues/muscles and shifts the weight to allow the toes to push the ground while walking or exercising. In this case, the volume, deformation and movement of the foot need to be taken into careful consideration in order to reduce the wrinkles and keep an optimum fit.

Example 1 has the center of the heel portion shifted towards the inside by 10% (approximately 1 cm in length) with respect to the 100% width W between the outer contour line and the inner contour line. Such a configuration is considered to make the fabric of the outside of the foot more relaxed, compared to the prior art. The inside of Example 1 has the same design as the prior art and is therefore relaxed similarly to the prior art. Due to the large volume and curvature of the outside of the foot, a change in the elongation percentage of the fabric of the outside of the foot is considered to have an impact on the wear comfort and compressed feeling.

Therefore, although the curved ankle portion on the instep side is likely to generate sagging (i.e., wrinkles) due to walking or exercising, and the heel portion is inevitably subjected to weight as the heel comes into contact with the ground, Example 1 is considered to be able to properly improve the fittability of the curved ankle portion on the instep side, lower the occurrence of sagging therein, and allow the heel portion to comfortably cover the heel.

What is claimed is:

1. A leg wear, comprising:
   a heel portion for covering a heel,
   wherein, in a state in which the leg wear is folded in a planar shape such that a sole of the leg wear is layered over an instep of leg wear when viewed from a sole side of the leg wear, a length A of a perpendicular line extending from a heel central point located at a center between a heel-side end of an outer gore line of the heel portion and a heel-side end of an inner gore line of the heel portion to an outer contour line is longer than a length B of a perpendicular line extending from the heel central point to an inner contour line, and
   wherein a length between the heel-side end and a lateral malleolus-side end of the outer gore line of the heel portion is 1.212 times to 1.368 times a length between the heel-side end and a medial malleolus-side end of the inner gore line of the heel portion.

2. The leg wear according to claim 1, wherein when a width W between the outer contour line and the inner contour line is assumed as 100% as viewed from the sole side of the leg wear folded in the planar shape, the length A of the perpendicular line from the heel central point to the outer contour line is 55% to 65%, and the length B of the perpendicular line from the heel central point to the inner contour line is 45% to 35%.

3. The leg wear according to claim 2, wherein a sole-side fabric width W1 and an instep-side fabric width W2 between the lateral malleolus-side end of the outer gore line of the heel portion and the medial malleolus-side end of the inner gore line of the heel portion are 100%, respectively.

4. The leg wear according to claim 1, further comprising: a toe portion for covering toes, wherein, as viewed from the sole side of the leg wear folded in the planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the contour line.

5. The leg wear according to claim 4, wherein when a width W between the outer contour line and the inner contour line is assumed as 100% as viewed from the sole side of the leg wear folded in the planar shape, the length C of the perpendicular line from the toe central point to the outer contour line is 55% to 65%, and the length D of the perpendicular line from the toe central point to the inner contour line is 45% to 35%.

6. A leg wear, comprising:
a heel portion for covering a heel, wherein, in a state in which the leg wear is folded in a planar shape such that a sole of the leg wear is layered over an instep of leg wear when viewed from a sole side of the leg wear, a length A of a perpendicular line extending from a heel central point located at a center between a heel-side end of an outer gore line of the heel portion and a heel-side end of an inner gore line of the heel portion to an outer contour line is longer than a length B of a perpendicular line extending from the heel central point to an inner contour line; and
a toe portion for covering toes, wherein, as viewed from the sole side of the leg wear folded in the planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the inner contour line, and
wherein a length between the toe-side end and an outer end of the outer gore line of the toe portion is 1.212 times to 1.368 times a length between the toe-side end and an inner end of the inner gore line of the toe portion.

7. The leg wear according to claim 4, wherein a length between the heel portion and the toe portion is increased in accordance with a difference between the length A of the perpendicular line from the heel central point to the outer contour line and the length B of the perpendicular line from the heel central point to the inner contour line, and a difference between the length C of the perpendicular line from the toe central point to the outer contour line and the length D of the perpendicular line from the toe central point to the inner contour line.

8. The leg wear according to claim 1, wherein a sole-side fabric width W1 and an instep-side fabric width W2 between the lateral malleolus-side end of the outer gore line of the heel portion and the medial malleolus-side end of the inner gore line of the heel portion are 100%, respectively.

9. The leg wear according to claim 1, further comprising:
a toe portion for covering toes,
wherein, as viewed from the sole side of the leg wear folded in the planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the inner contour line.

10. The leg wear according to claim 2, further comprising:
a toe portion for covering toes,
wherein, as viewed from the sole side of the leg wear folded in the planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the inner contour line.

11. The leg wear according to claim 3, further comprising:
a toe portion for covering toes,
wherein, as viewed from the sole side of the leg wear folded in the planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the inner contour line.

12. A leg wear, comprising:
a heel portion for covering a heel, wherein, in a state in which the leg wear is folded in a planar shape such that a sole of the leg wear is layered over an instep of leg wear when viewed from a sole side of the leg wear, a length A of a perpendicular line extending from a heel central point located at a center between a heel-side end of an outer gore line of the heel portion and a heel-side end of an inner gore line of the heel portion to an outer contour line is longer than a length B of a perpendicular line extending from the heel central point to an inner contour line; and
a toe portion for covering toes, wherein, as viewed from the sole side of the leg wear folded in the planar shape, a length C of a perpendicular line extending from a toe central point located at a center between a toe-side end of an outer gore line of the toe portion and a toe-side end of an inner gore line of the toe portion to the outer contour line is longer than a length D of a perpendicular line extending from the toe central point to the inner contour line, and
wherein when a width W between the outer contour line and the inner contour line is assumed as 100% as viewed from the sole side of the leg wear folded in the planar shape, the length C of the perpendicular line from the toe central point to the outer contour line is 55% to 65%, and the length D of the perpendicular line from the toe central point to the inner contour line is 45% to 35%, and
wherein a length between the toe-side end and an outer end of the outer gore line of the toe portion is 1.212 times to 1.368 times a length between the toe-side end and an inner end of the inner gore line of the toe portion.

13. The leg wear according to claim 5, wherein a length between the heel portion and the toe portion is increased in accordance with a difference between the length A of the perpendicular line from the heel central point to the outer contour line and the length B of the perpendicular line from the heel central point to the inner contour line, and a difference between the length C of the perpendicular line from the toe central point to the outer contour line and the length D of the perpendicular line from the toe central point to the inner contour line.

14. The leg wear according to claim 6, wherein a length between the heel portion and the toe portion is increased in accordance with a difference between the length A of the perpendicular line from the heel central point to the outer contour line and the length B of the perpendicular line from the heel central point to the inner contour line, and a difference between the length C of the perpendicular line from the toe central point to the outer contour line and the length D of the perpendicular line from the toe central point to the inner contour line.

* * * * *